United States Patent
Doherty et al.

(10) Patent No.: US 7,314,873 B2
(45) Date of Patent: Jan. 1, 2008

(54) (HALO-BENZO CARBONYL)HETEROBI CYCLIC P38 LINASE INHIBITING AGENTS

(75) Inventors: James B. Doherty, Montvale, NJ (US); Swaminathan R. Natarajan, Scotch Plains, NJ (US); John E. Stelmach, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 501 days.

(21) Appl. No.: 10/517,754

(22) PCT Filed: Jun. 6, 2003

(86) PCT No.: PCT/US03/17821

§ 371 (c)(1),
(2), (4) Date: Dec. 13, 2004

(87) PCT Pub. No.: WO03/103590

PCT Pub. Date: Dec. 18, 2003

(65) Prior Publication Data

US 2005/0176723 A1    Aug. 11, 2005

Related U.S. Application Data

(60) Provisional application No. 60/388,066, filed on Jun. 11, 2002.

(51) Int. Cl.
| | |
|---|---|
| A61K 31/5377 | (2006.01) |
| A61K 31/491 | (2006.01) |
| A61K 31/519 | (2006.01) |
| C07D 413/14 | (2006.01) |
| C07D 471/14 | (2006.01) |
| C07D 487/14 | (2006.01) |
| C07D 213/26 | (2006.01) |
| C07D 213/30 | (2006.01) |

(52) U.S. Cl. ............................. 514/234.5; 514/264.1; 514/252.14; 544/279; 544/117; 546/303; 546/334

(58) Field of Classification Search ............. 514/234.5, 514/252.14, 264.1; 544/279, 117
See application file for complete search history.

(56) References Cited

U.S. PATENT DOCUMENTS

2007/0078154 A1*  4/2007  Dinsmore et al. .......... 514/291

OTHER PUBLICATIONS

Bioorganic & Medicinal Chemistry Letters (2003), 13(2), 273-276.*
Hashimoto, et al.,J Pharmacol. and Experim. Therap., vol. 293, No. 2, pp. 370-375, 2000.*
Johnson, et al., Science, vol. 298 Dec. 6, 2002, 1911-1912.*
Schreiber, et al., Clin, Gastroenterol. Hepatol., 2006, Mar; 4(3):325-34 (PubMed abstract).*
Viral Defense Foundation, <http://www.viraldefense.org/mission.htm>, downloaded May 16, 2007.*
Visiting Nurse Assns. of America, <http://www.vnaa.org/vnaa/gen/Germ_Protection_Center_Cold_and_Flu_Resources,html...>, downloaded May 16, 2007.*
Boehm, Expert Opinion Therapeutic Patents (2000) 10(1), p 25.*
Dodeller, Arthritis Research & Therapy 2006, 8:205.*
Viral Defence Foundation, <http://www.viraldefence.org/mission.htm>, downloaded May 16, 2007.*
Visiting Nurse Assns. of America, <http://www.vnaa.org/vnaa/gen/Germ_Protection_Center_Cold_and_Flu_Resources, html...>, downloaded May 16, 2007.*

* cited by examiner

*Primary Examiner*—James O. Wilson
*Assistant Examiner*—Cecilia M. Jaisle
(74) *Attorney, Agent, or Firm*—Curtis C. Panzer; Valerie J. Camara

(57) ABSTRACT

Compounds described by the chemical formula (I) or pharmaceutically acceptable salts thereof: (I) are inhibitors of p38 and are useful in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation

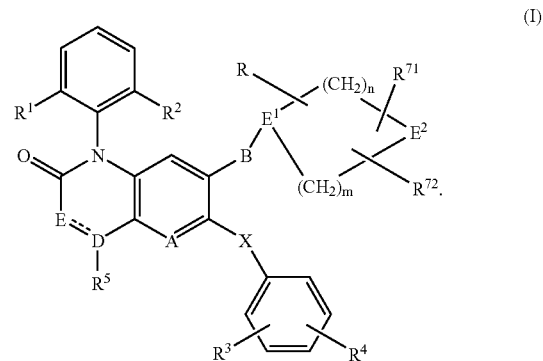

12 Claims, No Drawings

(HALO-BENZO CARBONYL)HETEROBI CYCLIC P38 LINASE INHIBITING AGENTS

RELATED APPLICATION DATA

This is a National filing under 35 USC 371 of PCT/US03/17821, filed Jun. 6, 2003, which claims priority from U.S. Ser. No. 60/388,066, filed Jun. 11, 2002.

BACKGROUND OF THE INVENTION

The present invention relates to heterobicyclic compounds that inhibit the action of the p38 mitogen-activated protein kinase, a mammalian protein kinase that is involved in cell proliferation, cell response to stimuli, and cell death. In particular, this invention relates to heterobicyclic compounds that are selective and potent inhibitors of the p38 mitogen-activated protein kinase. This invention also relates to pharmaceutical compositions containing such heterobicyclic compounds that inhibit the p38 mitogen-activated protein kinase.

Related Background

Mitogen-activated protein ("MAP") kinases mediate the surface-to-nucleus signal transduction in a cell. Protein kinases that activate and phosphorylate MAP are known as mitogen-activated protein kinase kinases ("MKK"). One such MKK specifically phosphorylates and activates the p38 MAP kinase ("p38") and is called MKK3. U.S. Pat. Nos. 5,736,381 and 5,804,427 describe human mitogen-activated kinase kinase isoforms. International Publication No. 98/00539 describes a human gene encoding an MKK3-Interacting Protein.

Xia et al., *Science*, 270, 1326-1331 (1995) describes the p38 signal transduction pathway as being activated by proinflammatory cytokines and environmental stress. MKK3 is described as being involved in transducing stress signals such as nerve growth factor mediated apaptosis in PC12 cells. It is believed that inhibition of p38 activity can provide relief from acute and chronic inflammation by blocking production of cytokines such as IL-1 and TNF, thereby inhibiting the production of proinflammatory cytokines such as IL-6 and IL-8. In particular, it is believed that p38 inhibitors block the synthesis of TNFα and IL-1β cytokines, thereby providing relief from inflammatory diseases such as arthritis. Accordingly, it would be desirable to provide novel compounds that are selective and potent inhibitors of the action of p38.

International Publication No. 97/22704 describes the mitogen-activated protein kinase kinase MEK6, which can stimulate phosphorylation and activation of p38 substrates. International Publication Nos. 95/31451, 99/00357 and 98/27098 describe various inhibitors of p38. Nonetheless, there remains a great need to develop inhibitors of the action of p38 for various pharmaceutical and therapeutic applications.

SUMMARY OF THE INVENTION

Compounds described by the chemical formula (I) or pharmaceutically acceptable salts thereof:

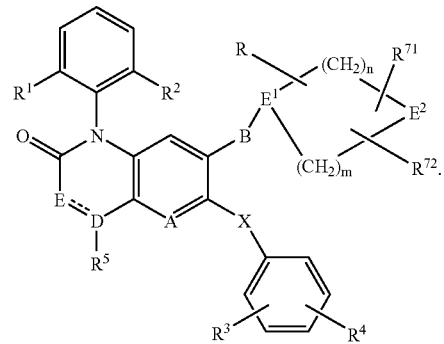

are inhibitors of p38.

DETAILED DESCRIPTION OF THE INVENTION

The present invention provides a compound that is an inhibitor of the action of p38, wherein the compound is described by the chemical formula (I), or a pharmaceutically acceptable salt thereof:

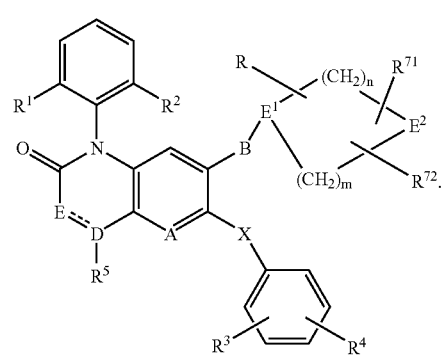

wherein
A is N, or CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
X is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
D is C or N;
E is N, O, NH, $CH_2$, or CH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH, N, or $CR^6$;

$E^2$ is CH2, CHR, NH, NR, O, S, —S(O)—, or —S(O)2—;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In one aspect, the present invention provides a compound described by the chemical formula (I), or a pharmaceutically acceptable salt thereof, wherein A is N;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
X is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
D is C or N;
E is N, O, NH, $CH_2$, or CH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —$N(CH_3)_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH, N, or $CR^6$;
$E^2$ is CH2, CHR, NH, NR, O, S, —S(O)—, or —S(O)2—;
$R^1$ is halogen or $C_{1-4}$alkyl;
$R^2$, $R^3$, $R^4$, and $R^6$ are each independently halogen, $C_{1-14}$alkyl, or hydrogen; and
$R^5$ is H, $CH_3$, or $CH_2CH_3$.

In a second aspect, the present invention provides a compound described by the chemical formula (I), or a pharmaceutically acceptable salt thereof, wherein A is N;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
X is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —$N(CH_3)_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH, N, or $CR^6$;
$E^2$ is CH2, CHR, NH, NR, O, S, —S(O)—, or —S(O)2—;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In a third aspect, the present invention provides a compound described by the chemical formula (I), or a pharmaceutically acceptable salt thereof, wherein A is N;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —$N(CH_3)_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH, N, or $CR^6$;
$E^2$ is CH2, CHR, NH, NR, O, S, —S(O)—, or —S(O)2—;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In a fourth aspect, the present invention provides a compound described by the chemical formula (1), or a pharmaceutically acceptable salt thereof, wherein A is N;
B is a direct bond;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —$N(CH_3)_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH, N, or $CR^6$;
$E^2$ is CH2, CHR, NH, NR, O, S, —S(O)—, or —S(O)2—;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In an embodiment of the fourth aspect, the present invention provides a compound described by the chemical formula (I), or a pharmaceutically acceptable salt thereof, wherein A is N;
B is a direct bond;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —$N(CH_3)_2$, or halogen;
n is 1, 2, 3, or 4;

m is 0, 1, 2, 3, or 4;
n+m is 2, 3, 4, 5, or 6;
$E^1$ is N;
$E^2$ is NR;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In another embodiment of the fourth aspect, the present invention provides a compound described by the chemical formula (I), or a pharmaceutically acceptable salt thereof, wherein
A is N;
B is a direct bond;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; one of n $CH_2$ and one of m $CH_2$ are bridged by a —$C_{0-2}$alkyl- linkage;
$E^1$ is N;
$E^2$ is NR;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In still another embodiment of the fourth aspect, the present invention provides a compound described by the chemical formula (I), or a pharmaceutically acceptable salt thereof, wherein
A is N;
B is a direct bond;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is N;
$E^2$ is O;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In yet another embodiment of the fourth aspect, the present invention provides a compound described by the chemical formula (I), or a pharmaceutically acceptable salt thereof, wherein
A is N;
B is a direct bond;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —H, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is N;
$E^2$ is CHR;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In a fifth aspect, the present invention provides a compound described by the chemical formula (I), or a pharmaceutically acceptable salt thereof, wherein
A is N;
B is —$C_{0-3}$alkyl-NH—$C_{0-3}$alkyl-;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH, N, or $CR^6$;
$E^2$ is CH2, CHR, NH, NR, O, S, —S(O)—, or —S(O)2—;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In an embodiment of the fifth aspect, the present invention provides a compound described by the chemical formula (I), or a pharmaceutically acceptable salt thereof, wherein
A is N;
B is —$C_{0-3}$alkyl-NH—$C_{0-3}$alkyl-;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —H, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH;
$E^2$ is NR;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In a sixth aspect, the present invention provides a compound described by the chemical formula (I), or a pharmaceutically acceptable salt thereof, wherein A is N;
B is —$C_{0-3}$alkyl-O—$C_{0-3}$alkyl-;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH, N, or $CR^6$;
$E^2$ is CH2, CHR, NH, NR, O, S, —S(O)—, or —S(O)2—;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

In an embodiment of the sixth aspect, the present invention provides a compound described by the chemical formula (I), or a pharmaceutically acceptable salt thereof, wherein A is N;
B is —$C_{0-3}$alkyl-O—$C_{0-3}$alkyl-;
X is —$C_{0-3}$alkyl-S—$C_{0-3}$alkyl-;
D is C;
E is NH;
R, $R^{71}$, and $R^{72}$ each independently is hydrogen, OH, —$C_{0-4}$alkyl-O—$C_{0-4}$alkyl-, —$C_{0-4}$alkyl-C(O)—$C_{0-4}$alkyl-, —$C_{0-4}$alkyl-C(O)—O—$C_{0-4}$alkyl-, or $C_{1-4}$alkyl, any alkyl optionally substituted with 1-6 groups, each group independently being —OH, —$NH_2$, —NH—$CH_3$, —N($CH_3$)$_2$, or halogen;
n is 1, 2, 3, or 4;
m is 0, 1, 2, 3, or 4;
n+m is 2, 3, 4, 5, or 6; optionally, one of n $CH_2$ and one of m $CH_2$ are bridged by a —$C_{0-2}$alkyl- linkage;
$E^1$ is CH;
$E^2$ is NR;
$R^1$ is halogen or $C_{1-4}$alkyl;
$R^2$, $R^3$, $R^4$, and $R^6$ are each independently halogen, $C_{1-4}$alkyl, or hydrogen; and
$R^5$ is H, $CH_3$, or $CH_2CH_3$.

The compounds of the present invention are prepared by the following illustrative schemes:

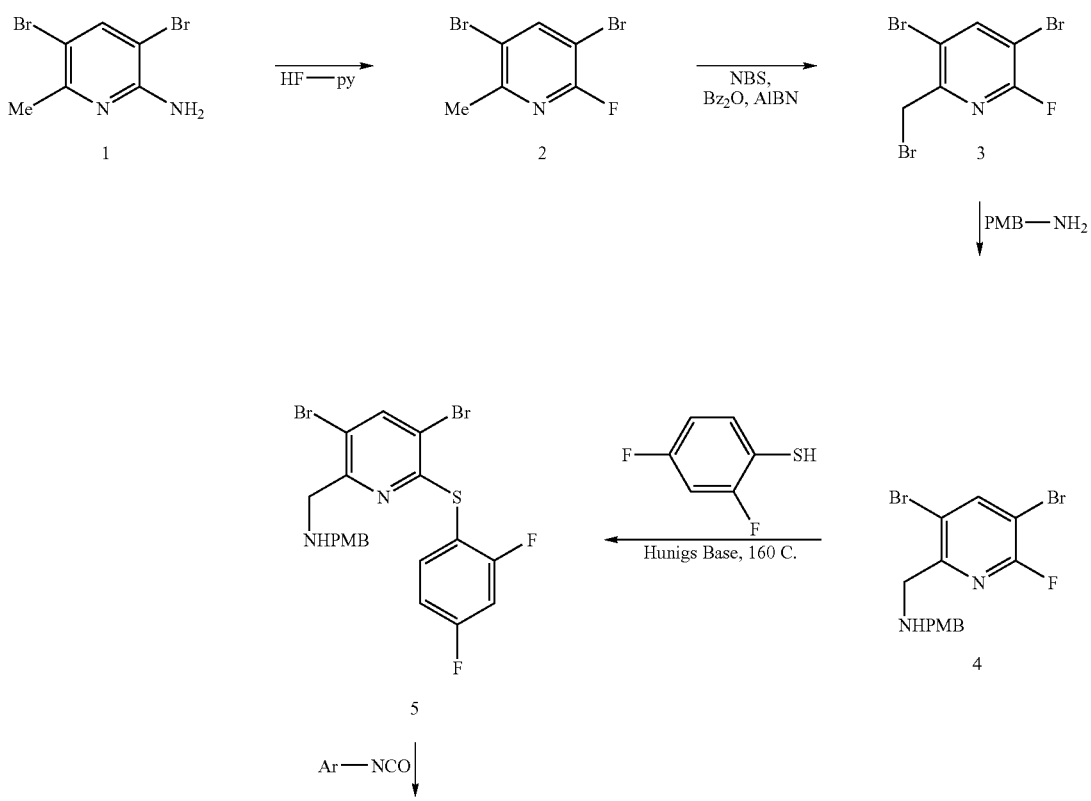

Scheme 1

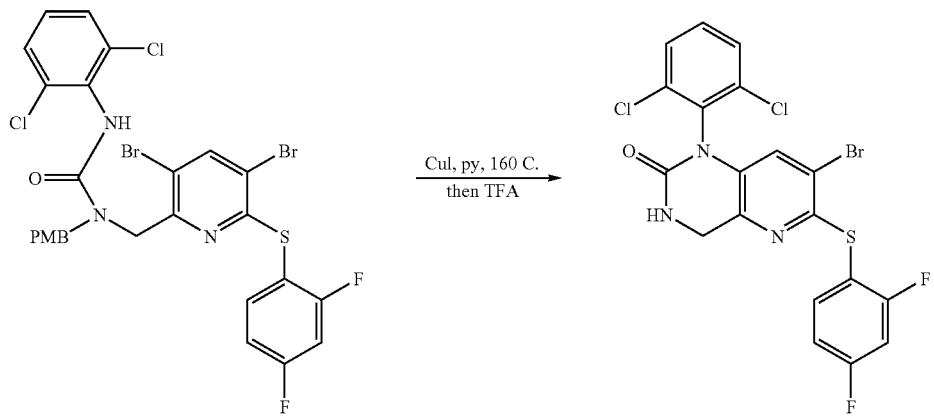

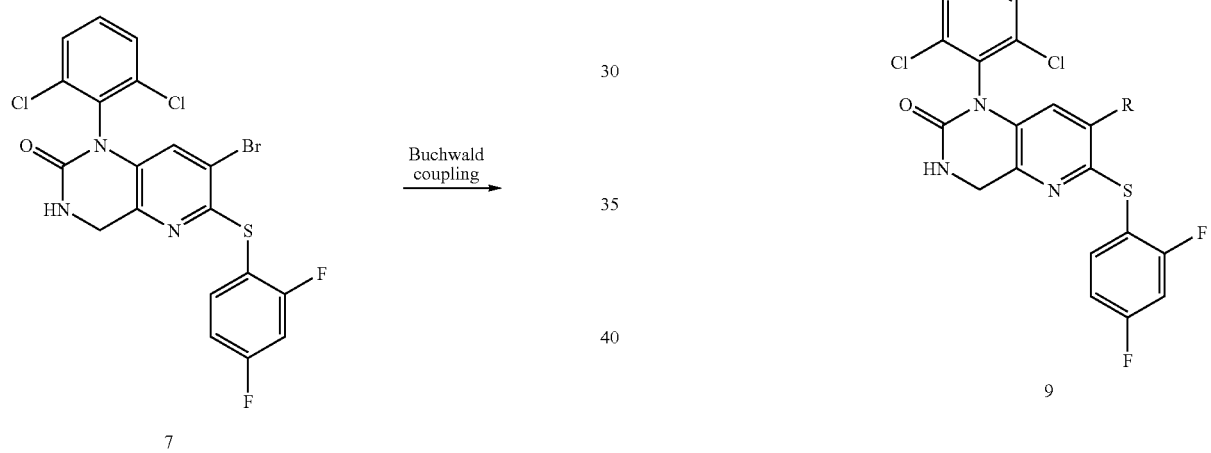

As used herein, "alkyl" as well as other groups having the prefix "alkyl" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzo-fused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

The term "$C_0$-$C_6$alkyl" includes alkyls containing 6, 5, 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The heteroatoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, perhydroazepinyl, piperazinyl, morpholinyl, tetrahydrofuranyl, imidazolinyl, pyrolidin-2-one, piperidin-2-one, and thiomorpholinyl.

The term "N-heterocyclo$C_{4-7}$alkyl" describes nonaryl heterocyclic compounds having 3-6 carbon atoms and one nitrogen atom forming the ring. Examples include azetidinyl, pyrrolidinyl, piperidinyl, and perhydroazepinyl.

Examples of aryl($C_{1-6}$)alkyl include, for example, phenyl($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)OC$_1$-C$_4$alkyl, and -OC(O)NHC$_1$-C$_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$) alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Unless specifically stated otherwise or indicated by a bond symbol (dash or double dash), the connecting point to a recited group will be on the right-most stated group. That is, for example, a phenylalkyl group is connected to the main structure through the alkyl and the phenyl is a substituent on the alkyl.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol,ethanolamine, ethylenediamine, N-ethyl glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound described by Formula (I), or a pharmaceutically acceptable salt thereof, in combination with a pharmaceutically acceptable carrier.

The invention described herein also includes a pharmaceutical composition which is comprised of a compound described by Formula (I), or a pharmaceutically acceptable salt thereof, in combination with a pharmaceutically acceptable carrier. The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists.

The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention includes methods of treating arthritis by administering to a mamalian patient in need of such treatment a compound described by Formula (I), or a pharmaceutically acceptable salt thereof, in combination or in coadministration with a COX-2 inhibitor.

The invention described herein also includes a method of treating a cytokine mediated disease in a mammal, comprising administering to a mammalian patient in need of such treatment an amount of a compound described by Formula (I), or a pharmaceutically acceptable salt thereof, in an amount which is effective to treat said cytokine mediated disease.

Of particular interest is a method of treating inflammation in a mammalian patient in need of such treatment, which is comprised of administering to said patient an anti-inflammatory effective amount of a compound described by Formula (I), or a pharmaceutically acceptable salt thereof.

Another method which is of particular interest is a method of treating a cytokine mediated disease as described herein wherein the disease is osteoporosis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of treating arthritis in a mammal in need such treatment, which comprises administering to said mammal an amount of a compound of formula I which is effective for treating arthritis. Such method includes the treatment of rheumatoid and osteoarthritis.

When administered to a patient for the treatment of athritis, the dosage used can be varied depending upon the type of arthritis, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

This invention also relates to a method of inhibiting the action of p38 in a mammal in need thereof, which comprises administering to said mammal an effective amount of a compound described by Formula (I), or a pharmaceutically acceptable salt thereof, to inhibit said action of p38, down to normal levels, or in some cases to subnormal levels, so as to ameliorate, prevent or treat the disease state.

The compounds of formula 1 can be used in the prophylactic or therapeutic treatment of disease states in mammals which are exacerbated or caused by excessive or unregulated cytokines, more specifically IL-1, IL-6, IL-8 or TNF.

Because the compounds of formula I inhibit cytokines, such as IL-1, IL-6, IL-8 and TNF, by inhibiting the action of p38 the compounds are useful for treating diseases in which cytokine presence or activity is implicated, such as pain, rheumatoid arthritis, rheumatoid spondylitis, osteoarthritis, gouty arthritis and other arthritic conditions.

The compounds described by Formula (I), or a pharmaceutically acceptable salt thereof, are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds described by Formula (I), or a pharmaceutically acceptable salt thereof, are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds described by Formula (I), or a pharmaceutically acceptable salt thereof, are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound described by Formula (I), or a pharmaceutically acceptable salt thereof, in an amount which is effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment are preferably carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Assays

Protein Expression and Purification.

Murine p38 containing the FLAG epitope tag was expressed in *Drosophila* S2 cells under transcriptional control of a copper-inducible metallothionein promoter. Expression of recombinant p38 was induced by treating transfected cells with 1 mM $CuSO_4$ for 4 hours. To generate active recombinant murine p38, $CuSO_4$-treated S2 cells were stimulated 10 minutes prior to harvest with 400 mM NaCl, 2 mM $Na_3VO_4$, and 100 μg/L okadaic acid. Cell pellets were washed with phosphate-buffered saline, 2 mM $Na_3VO_4$, and lysed in 20 mM Tris HCl, pH 7.5, 120 mM NaCl, 1% Triton X-100, 2 mM EDTA, 20 mM NaF, 4 mM $Na_3VO_4$, 2 mM Prefabloc SC (Boehringer Mannheim). Cell lysates were centrifuged for 10 min at 13,000×g, and activated, recombinant murine p38 was immunoaffinity purified from the lysate by column chromatography through anti-FLAG M2 resin (Kodak) that had been equilibrated with lysis buffer. After loading the extract the resin was washed with 10 column volumes of lysis buffer, 10 column volumes buffer A (10 mM Tris HCl, pH 7.5, 500 mM NaCl, 20% glycerol) and 10 column volumes of buffer B (10 mM Tris HCl pH 7.5, 150 mM NaCl, 20% glycerol). The fusion protein was eluted in buffer B containing 100 μg/mL FLAG peptide (Kodak).

The N-terminal 115 amino acids of ATF-2 was expressed in *E. coli* as a fusion protein with glutathione-S-transferase. The fusion protein was purified over glutathione agarose according to standard procedures (Pharmacia).

p38 Kinase Assay.

p38 kinase assays were performed in a reaction volume of 100 μL in a 96-well plate, at 30° for 45–1200 min under the following conditions: 25 mM Hepes, pH 7.4, 10 mM $mgCl_2$, 20 mM β-glycerolphosphate, 2 mM DTT, 5 μM ATP, 10 μCi [γ-$^{33}$P]-ATP and ~2 μM GST-ATF2. Serial dilutions of compounds were added to each reaction in 2 μL DMSO. 2 μL of DMSO was added to the last row of each reaction plate as the no inhibitor control for each inhibitor titration. The reaction was terminated with an equal volume of a stop solution containing 100 mM EDTA and 15 mM sodium pyrophosphate. PVDF filter plates (MAIPNOB50, Millipore) were pre-wet with methanol and washed with the stop solution. 50 μL aliquots from a single reaction were applied to the filter under vacuum, and the filter was washed twice with 75 mM phosphoric acid. The filter plates were counted in a scintillation counter (Top Count, Packard) and the percent inhibition at each compound concentration is determined.

TNF-α Release Assay.

Blood was obtained from healthy volunteers by venipuncture using sodium heparin as an anti-coagulant. Peripheral blood mononuclear cells (PBMCs) were isolated using Lymphocyte Separation Medium (ICN) according to manufacturers specifications. Isolated PBMCs were washed 3 times with HBSS and diluted to a density of 2×10$^6$ cells/mL in RPMI+5% autologous human serum. 50 μL of the serial dilutions of inhibitor were added to wells of a 96-well tissue culture plate followed by addition of 100 μL of PBMCs and then 50 μL of RPMI complete medium containing 400 ng/mL LPS. A control well of cells without compound but with LPS (maximal stimulation control) and one without compound and without LPS (background control) were included in each titration. The cells were incubated for 16 hours in a humidified incubator at 37° C., 5% $CO_2$. Supernatants were then harvested and TNF-α levels were quantified by immunoassay using commercial reagents (R&D, Inc).

The compounds of this invention demonstrated efficacy in the above assays by results of less than 10 μM. Advantageous compounds had results less than 1 μM. Even more advantageous compounds had results less than 0.1 μM. Still more advantageous compounds had results in the assays of less than 0.01 μM.

The abbreviations used herein are as follows unless specified otherwise:

| | |
|---|---|
| $BH_3$*THF | Tetrahydrofuran/borane complex |
| BINAP | 2,2'-Bis(diphenylphosphino)-1,1'-binaphthyl |
| BOC | t-Butoxycarbonyl |
| $BOC_2O$ | t-Butoxycarbonyl anhydride |
| CBZ | Carbobenyloxy |
| CBZ-Cl | Carbobenzyl chloride |
| DCM | Dichloromethane |
| DIPEA | Diisopropylethylamine |
| DMAP | 4-Dimethylaminopyridine |
| DMF | N,N-Dimethylformamide |
| DMF-DMA | Dimethylformamide-Dimethylacetal |
| DMSO | Dimethylsulfoxide |
| EDC | 3-Ethyl-3-(3-dimethylaminopropyl)carbodiimide hydrochloride |
| h | hours |
| HOAt | 1-Hydroxy-7-azabenzotriazole |
| HOBt | Hydroxybenzoxazole |
| IPA | Isopropanol |
| mCPBA | meta Chloroperbenzoic acid |
| min | minutes |
| MeCN | Acetonitrile |
| NMR | nuclear magnetic resonance |
| r.t., RT, or rt | room temperature |
| sat. | saturated |
| TEA | Triethylamine |
| TFA | Trifluoroacetic acid |
| THF | Tetrahydrofuran |

EXAMPLES

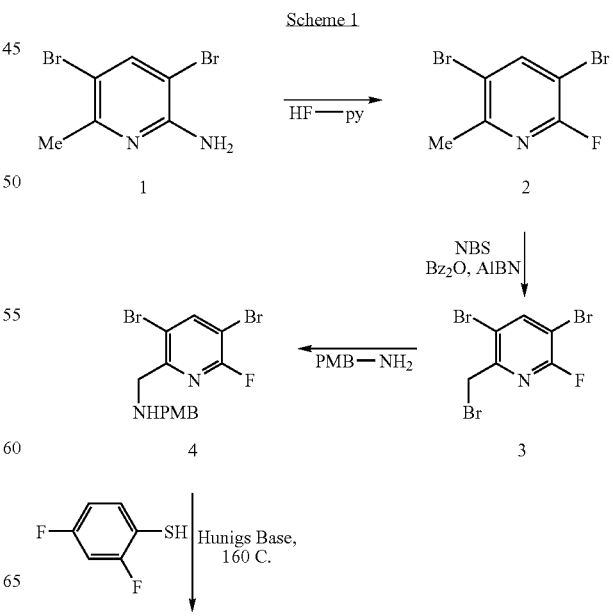

Scheme 1

-continued

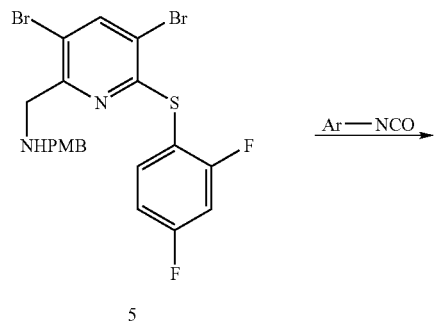

5

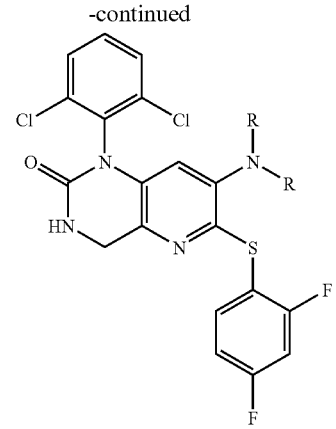

8

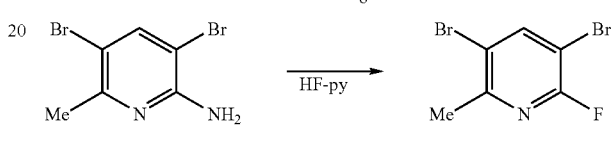

To a stirred solution of 2-amino-3,5-dibromo-6-methylpyridine (25.0 g 0.094 moles) in HF•pyridine (50 mL) was added NaNO₂ (9.73 g, 0.141 moles) slowly at −10° C. Reaction was stirred until complete by TLC. Reaction mixture was diluted with 150 mL of dichloromethane. The resulting organic phase was back extracted three times with 100 L of water. The organic phase was dried over sodium sulphate and concentrated. Resulting oil was subjected to flash chromatography (gradient: 0-20% ether in hexanes) and resulted in the fluorinated compound 2. 1H NMR (CDCl, 500 MHz, ppm) 8.05 (1H, d, 4 Hz); 2.6 (3H, s)

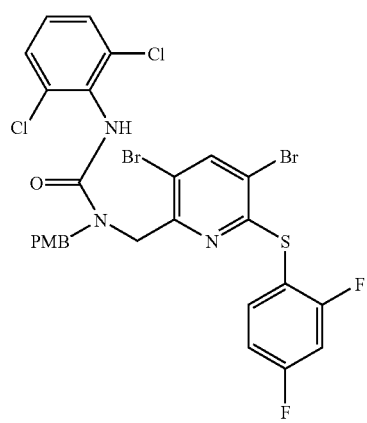

6

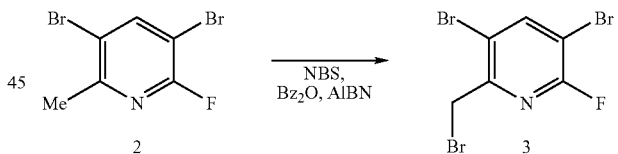

To a stirred solution of 2 (24 g, 0.0895 moles) in 500 mL of CCl₄ was added NBS (22.3 g, 0.125 moles) and benzoyl peroxide (2.16 g, 8.95 mmoles). The reaction mixture was degassed by evacuation and purging with argon several times. The reaction was heated to reflux under inert atmosphere. Once at reflux, AIBN (1.51 g, 8.95 mmoles) is added. Reaction was heated until complete by TLC (usually 12 h). The reaction mixture was then cooled to rt and concentrated to half volume and filtered over a plug of silicagel. The silica gel plug was further eluted with a 20% ether in hexanes (1L). The combined organic phases was concentrated under reduced presure resulting in 34 g of brominated compound 2 which was used in the next step directly. 1H NMR (CDCl, 500 MHz, ppm) 8.16 (1H, d, 4 Hz); 4.6 (3H, s)

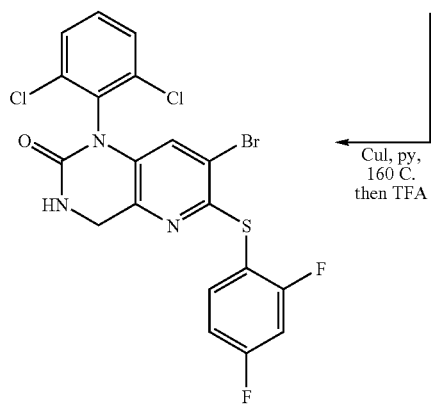

7

1. 2 equiv. of amine, 1.1 equiv of NaOtBu, 0.2 equiv. of BINAP, 0.1 equiv of Pd₂(dba)₃, dioxane, 100° C. 8 h. Buchwald coupling
2. deprotection with TFA where necessary

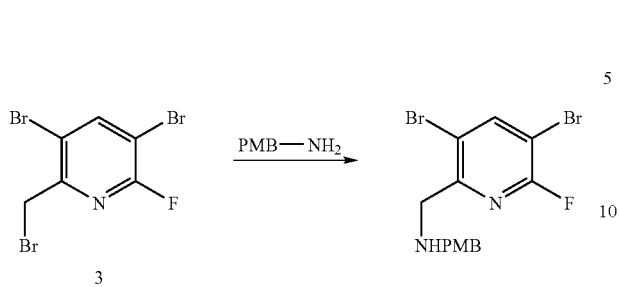

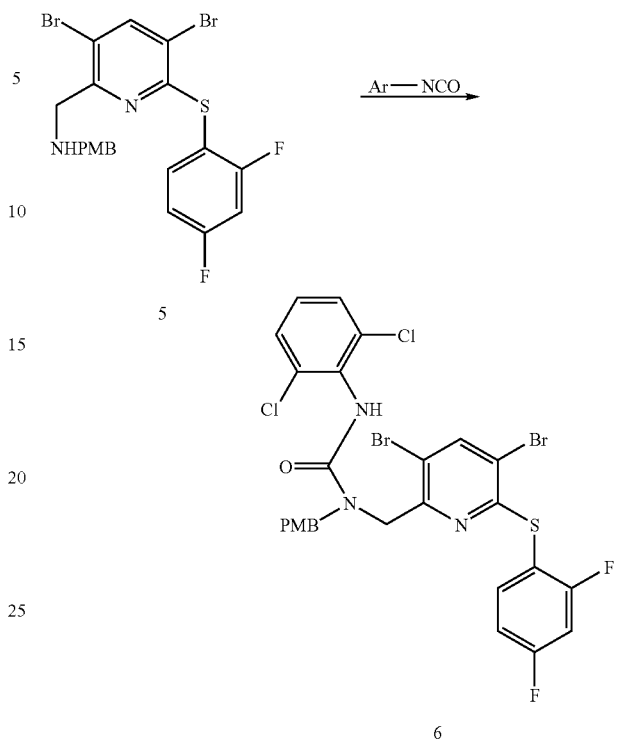

To a stirred solution of para-methoxy benzyl amine (34 g, 97.75 mmoles) and triethylamine (9.91 g, 97.93 mmoles) in 200 mL of dichloromethane at −10° C., a 500 mL solution of 2 (89.5 mmoles) in dicloromethane was added dropwise (over 2 h). The reaction was stirred at this temperature (ca 12 h) until starting material was consumed, as observed by TLC. The reaction mixture was washed twice with brine (100 mL) and dried over sodium sulphate. The organic phase was filtered and concentrated to give a viscous oil. The residue was purified by flash column chromatography (gradient: 0-40% ethyl acetate in hexanes) to give compound 4. 1H NMR (CDCl, 500 MHz, ppm) 8.08 (1H, d, 4 Hz); 7.28 (2H, d, 8.5 Hz); 6.88 (2H, d, 8.5 Hz); 3.94 (2H, s); 3.82 (3H, s); 3.79 (2H, s). MS: [M+H]=402

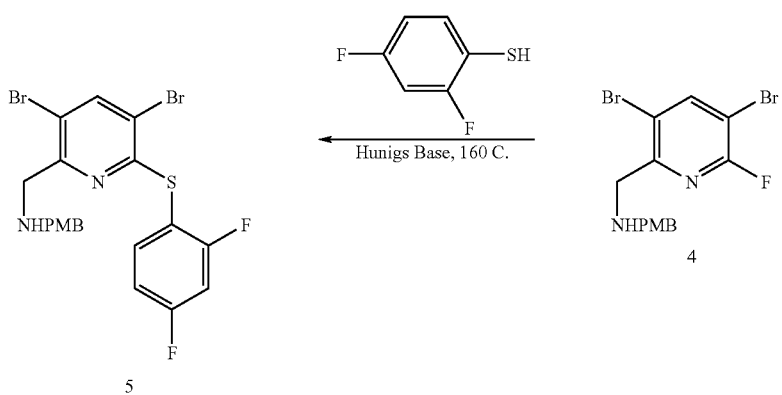

To a stirred, deoxygenated, solution of compound 4 (4.0 g, 9.90 mmoles) in 10 mL of dioxane was added 2,4 difluoro thiophenol (1.76 g, 11.80 mmoles). Then N,N-Diisopropylethylamine (2.55 g, 19.73 mmoles) was added and the reaction was heated under argon at 100° C. overnight. After 12 h, TLC showed complete consumption of starting material. The reaction mixture was diluted with 20 mL of ethylacetate and 10 mL of 5% sodium hydroxide solution. The organic phase was separated and washed with 10 mL of brine twice, dried over sodium sulphate and concentrated to give a viscous oil. The residue was purified by flash column chromatography (gradient: 0-40% ethyl acetate in hexanes) and product 5 was obtained. 1H NMR (CDCl, 500 MHz, ppm) 7.88 (1H, s); 7,5 (1H, m); 7.1 (2H, d, 8.5 Hz); 6.8 (2H, d, 8.5 Hz); 6.83 (1H, m); 6.70 (1H, m); 3.85 (3H, s); 3.80 (2H, s); 3.55 (2H, bs). MS: [M+H]=529

To a stirred solution of 5 (16 g 0.0397 moles) in 50 mL of dry CH$_2$Cl$_2$ was added 2,6-dichlorophenyl isocyanate (8.95 g, 0.0476 moles). Reaction was stirred until complete by TLC. The reaction was diluted with 100 mL of dichloromethane and washed with 50 mL of brine. The organic phase was collected, dried over sodium sulphate and concentrated to a solid residue. The residue was triturated in a solution of 40% ether in hexanes. Filteration then provided the required urea 6. 1H NMR (CDCl, 500 MHz, ppm) 7.99 (1H, s); 7.45 (1H, m); 7.32-7.36 (3H, m); 7.22 (2H, d, 8.5 Hz); 7.13 (1H, t, 7 Hz); 6.9 (2H, d, 8.5 Hz); 6.84-6.92 (2H, m); 4.50 (2H, bs); 4.49 (2H, s); 3.81 (3H, s). MS: [M+H]=716

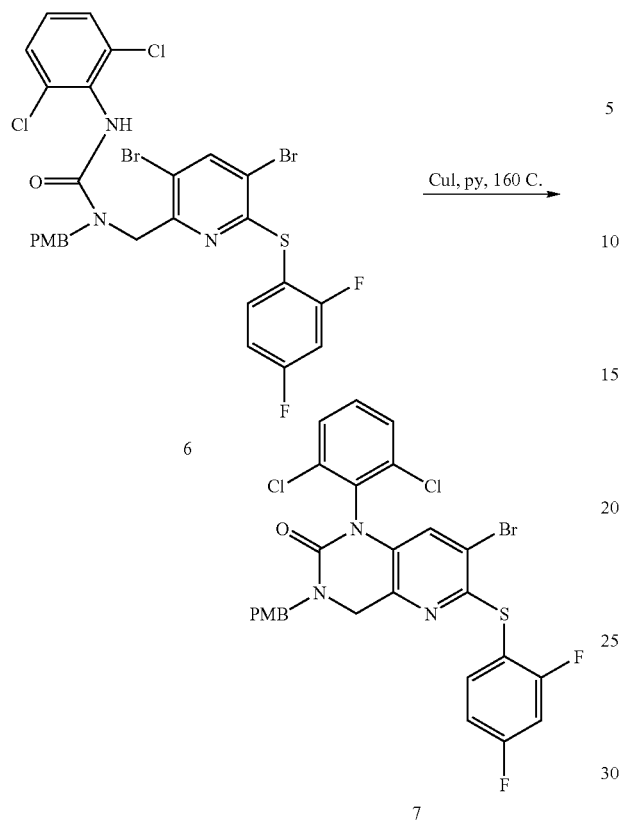

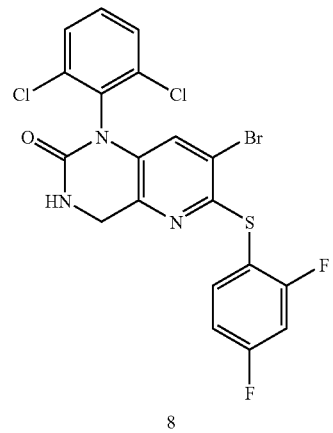

To a stirred, deoxygenated solution of 6 (1.0 g, 1.69 mmoles) in 5 mL of pyridine was added dry $K_2CO_3$ (700 mg, 5.07 mmoles) and CuI (641 mg, 3.37 mmoles). The reaction was heated to 160° C. for 30 min. TLC analysis at this point indicated complete concumption of starting material. The reaction mixture was filtered. The residue was washed with dichloromethane. The combined organic phases were collected and concentrated to a solid residue. The crude was re-dissolved in 50 mL of ethyl acetate and washed with dilute ammonium hydroxide (20 mL×3) followed by an extraction with brine (20 mL). The organic phase was dried over sodium sulphate, concentrated and the residue was purified by flash column chronatography (gradient: 0-40% ethyl acetate in hexanes) to provide the cyclized urea 7. 1H NMR (CDCl, 500 MHz, ppm) 7.47-7.55 (3H, m); 7.42 (1H, t, 7 Hz); 7.28 (2H, d, 8.5 Hz); 6.84-6.96 (4H, m); 4.60 (2H, s); 4.25 (2H, s); 3.8 (3H, s). MS: [M+H]=636

Compound 7 (501 mg, 0.785 mmoles) was dissolved in 15 mL of trifluoro acetic acid. The reaction mixture was brought to reflux and stirred at that temperature for 12 h. TLC analysis indicated complete consumption of starting material. The rection mixture was cooled to rt and then evaropated to dryness. The residue was taken up in 35 mL of ethyl acetate and extracted with 15 mL of saturated sodium bicarbonate solution followed by extraction with 155 mL of brine. The combined organic phases were dried over sodium sulphate and concentrated. The resulting residue was purified by flash column chromatography (gradient: 0-80% ethyl acetate in hexanes) to provide compound 8. 1H NMR (CDCl, 500 MHz, ppm) 7.53 (3H, m); 7.42 (1H, t, 7 Hz); 6.96 (2H, m); 6.5 (1H, s); 5.18 (1H, bs); 4.42 (2H, s). MS: [M+H]=517.

General Procedure for Buchwald Couplings

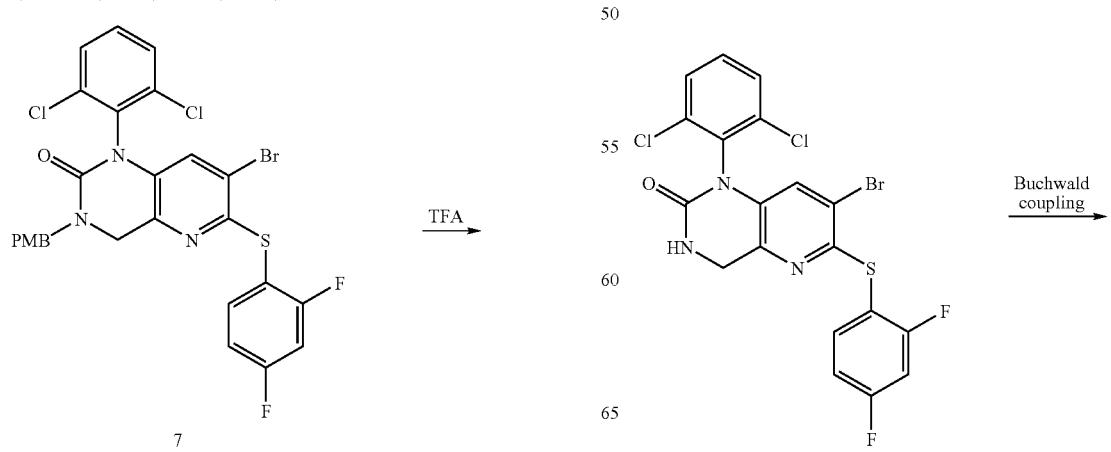

-continued

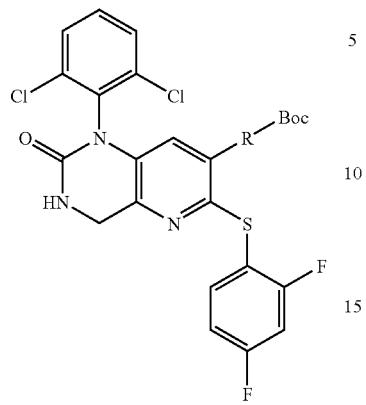

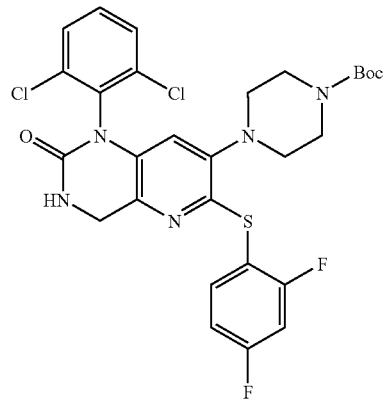

EX. 1

A flame dried round bottomed flask was charged with Pd2(DBA)3 (1 mmole) and BINAP (2 mmole). Deoxygenated toluene (5 mL) was added and the reaction mixture was evacuated and back filled with argon. The reaction mixture was heated under an argon atmosphere, in oil bath at 40° C. After 20 min heating, a clear homogenous solution resulted. The reaction mixture was brought to rt and charged with sodium t-butoxide (10 mmole) and the amine to be coupled (12 mmole) followed by addition of the aryl bromide (10 mmole) as a solution in 30 mL of toluene. The reaction mixture was carefully evacuated and back filled with argon a few times. The reaction mixture was heated under argon at 80° C. for 12 h. TLC analysis was used to measure the consumption of starting material. The reaction mixture was diluted with 80 mL of ethyl acetate and extracted with brine (50 mL×3). The organic phase was dried over sodium sulphate and concentrated. The residue was purified by flash column chromatography (gradient: 0-7% methanol in dichloromethane) to provide desired coupled products.

1H NMR (CDCl, 500 MHz, ppm) 7.56-7.48 (3H, m); 7.41 (1H, t); 6.94 (2H, m); 5.89 (1H, s); 5.22 (1H, bs); 4.48 (2H, bs); 3.58 (4H, m); 2.83 (4H, m); 1.46 (9H, s). MS: [M+H]=622.

Example 2

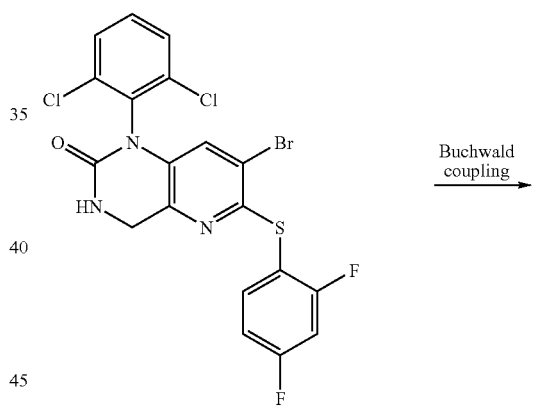

Example 1

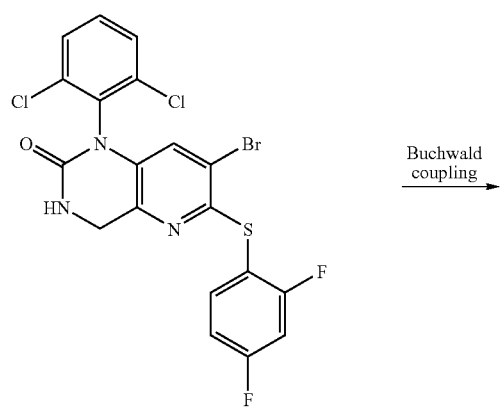

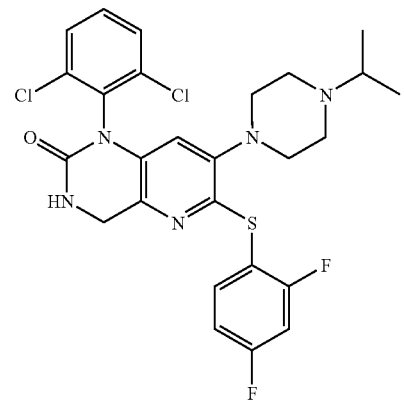

The amine coupling partner was commercially available 4-N-isopropyl-piperazine. Following the described general procedure the desired compound was obtained; 1H NMR (CDCl, 500 MHz, ppm) 7.56-7.48 (3H, m); 7.41 (1H, t); 6.94 (2H, m); 5.89 (1H, s); 5.22 (1H, bs); 4.50 (2H, s); 3.15 (1H, m); 2.90 (4H, m); 2.7 (4H, m); 1.62 (6H, bs). MS: [M+H]=564.

Example 3

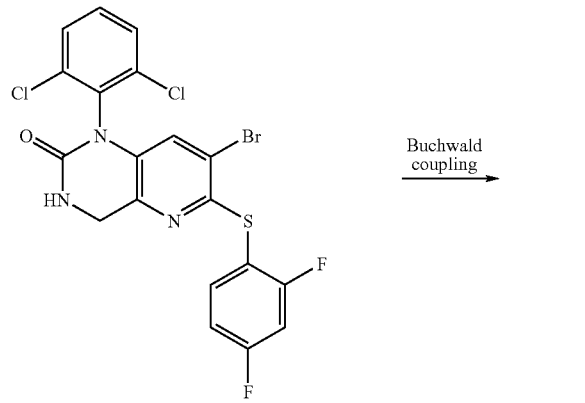

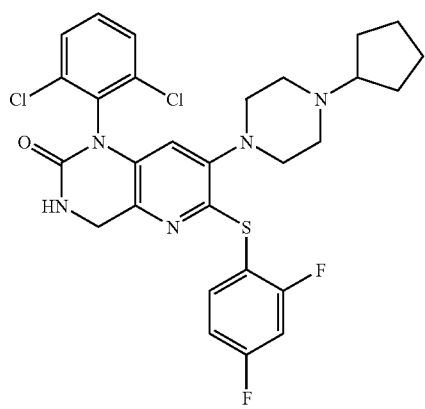

The amine coupling partner was commercially available 4-N-cyclopentyl-piperazine. Following the described general procedure the desired compound was obtained; 1H NMR (CDCl, 500 MHz, ppm) 7.56-7.48 (3H, m); 7.41 (1H, t); 6.94 (2H, m); 5.89 (1H, s); 5.22 (1H, bs); 4.50 (2H, s); 3.7 (2H, m); 3.35 (5H, m); 3.05 (2H, m); 1.4-2.2 (8H, m). MS: [M+H]=591.

Example 4

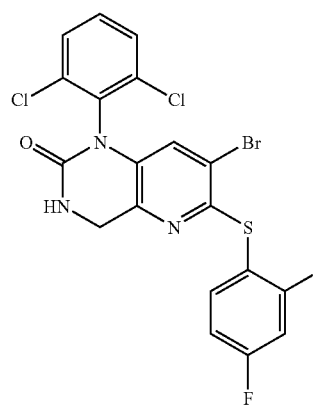

-continued

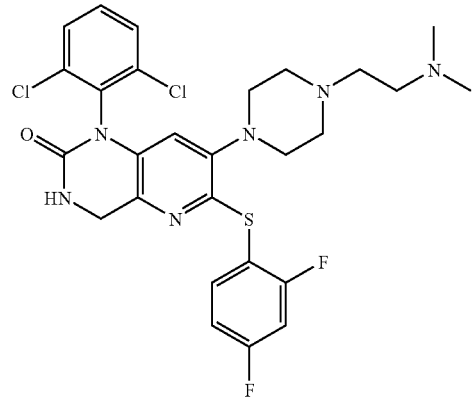

The amine coupling partner was commercially available 4-N-(2-N'-dimethyl amino-ethyl)-piperazine. Following the described general desired compound was obtained; 1H NMR (CDCl, 500 MHz, ppm) 7.56-7.48 (3H, m); 7.41 (1H, t); 6.94 (2H, m); 5.89 (1H, s); 5.22 (1H, bs); 4.50 (2H, s); 2.0-3.0 (18H). MS: [M+H]=593

Example 5

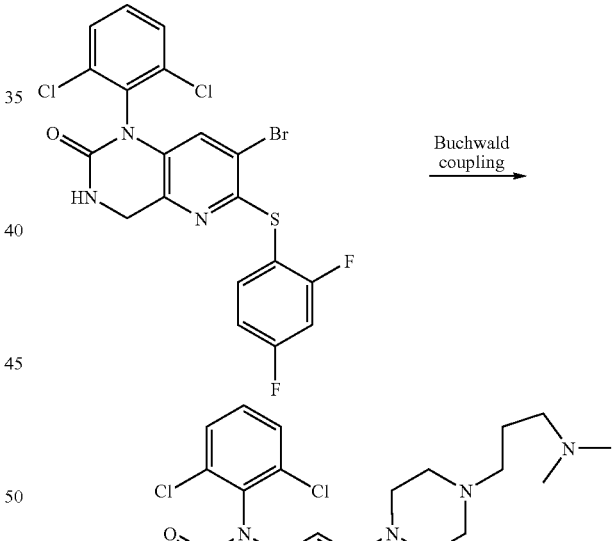

The amine coupling partner was commercially available 4-N-(3-N'-dimethyl amino-propyl)-piperazine. Following the described general desired compound was obtained; 1H NMR (CDCl, 500 MHz, ppm) 7.56-7.48 (3H, m); 7.41 (1H, t); 6.94 (2H, m); 6.02 (1H, s); 5.30 (1H, bs); 4.50 (2H, s); 2.91 (6H, m); 2.6 (66H, m); 2.45 (6H, bs); 1.85 (2H, m). MS: [M+H]=607.

Example 6

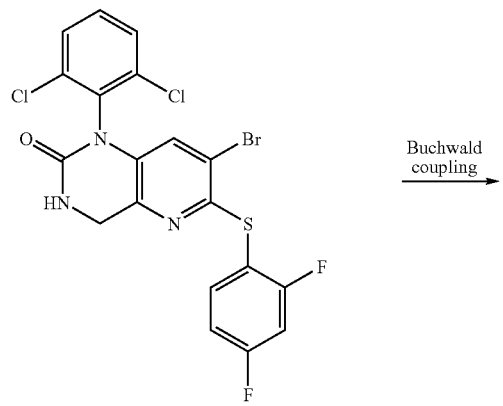

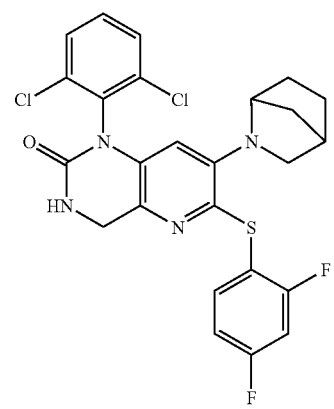

The amine coupling partner was commercially available adamantyl amine. following the described general procedure the desired compound was obtained; 1H NMR (CDCl, 500 MHz, ppm) 7.52 (2H, m); 7.37 (1H, t, J=7 Hz); 7.26 (1H, m); 6.85 (2H, m); 5.65 (1H, s); 5.4 (1H, bs); 4.52 (2H, bs); 3.78 (1H, bs); 3.68 (1H, dd, J=8 Hz and 3.5 Hz); 2.83 (1H, d, J=8 Hz); 2.52 (1H, m); 1.28-1.72 (6H, m). MS: [m+H]=533

Example 7

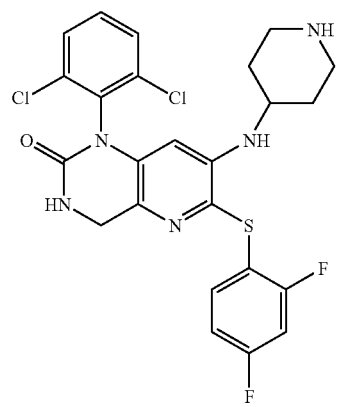

The amine coupling partner was commercially available 4-amino-piperidine. Following the described general procedure the desired compound was obtained; 1H NMR (CDCl, 500 MHz, ppm) 7.48 (2H, d, J=8 Hz); 7.36 (1H, t, J=8 Hz); 7.26 (1H, m); 6.8 (2H, m); 5.46 (1H, s); 4.6 (3H, bs); 3.0 (2H, m); 2.95 (1H, m); 2.56 (2H, m); 1.8 (2H, m); 1.32 (2H, m). MS: [M+H]=536.

Example 8 AND Example 9

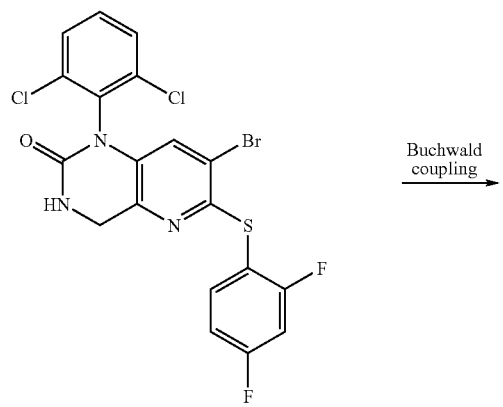

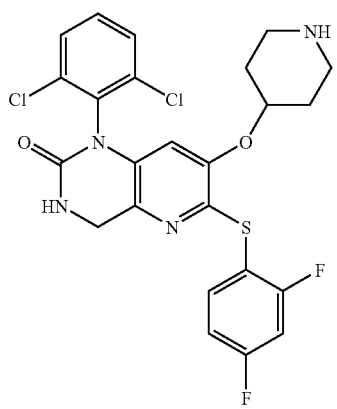

+

-continued

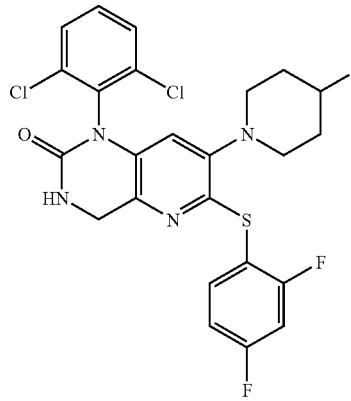

The amine coupling partner was commercially available 4-hydroxy-piperidine. Following the described general procedure, the desired compound EXAMPLE 8 was obtained along with equal amount of its regiomer EXAMPLE 9;

Example 8

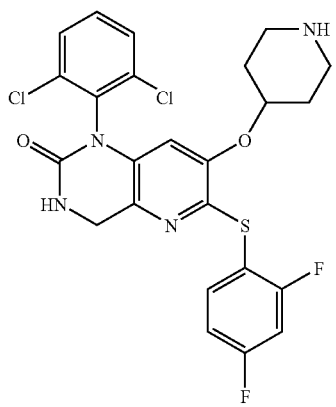

1H NMR (CDCl, 500 MHz, ppm) 7.52 (3H, m); 7.4 (1H, t, J=8 Hz); 6.92 (2H, m); 5.98 (1H, s); 5.52 (1H, bs); 4.87 (1H, m); 4.5 (2H, s); 3.08 (2H, m); 2.73 (2H, m); 2.2 (2H, m); 1.86 (2H, m). MS: [M+H]=538.

Example 9

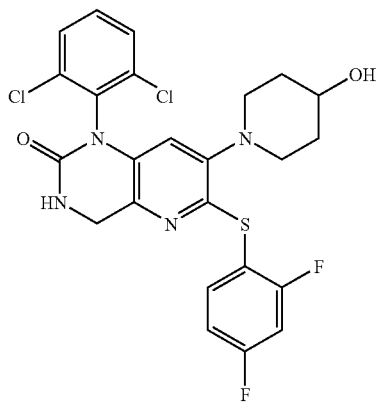

1H NMR (CDCl, 500 MHz, ppm) 7.52 (3H, m); 7.4 (1H, t, J=8 Hz); 6.92 (2H, m); 6.02 (1H, s); 5.22 (1H, bs); 4.5 (2H, s); 3.92 (2H, m); 3.15 (2H, m); 2.73 (2H, m); 2.02 (2H, m); 1.75 (2H, m). MS: [M+H]=538.

Example 10

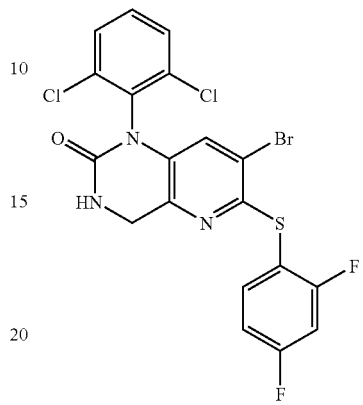

The amine coupling partner was commercially available 2,6-dimethyl-morpholine. Following the described general procedure the desired EXAMPLE 10 was obtained; 1H NMR (CDCl, 500 MHz, ppm) 7.48-7.56 (3H, m); 7.42 (1H, t, J=8 Hz); 6.93 (2H, m); 5.95 (1H, s); 5.15 (1H, bs); 4.51 (2H, bs); 3.85 (2H, m); 3.06 (2H, m); 3.04 (2H, m). MS: [M+H]=551.

Example 11

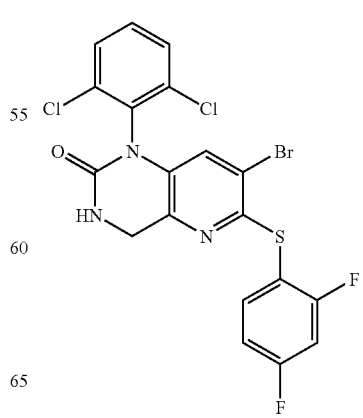

-continued

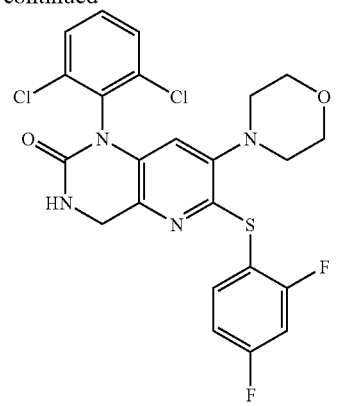

The amine coupling partner was commercially available morpholine. Following the described general procedure the desired compound was obtained; 1H NMR (CDCl, 500 MHz, ppm) 7.48-7.56 (3H, m); 7.42 (1H, t, J=8 Hz); 6.93 (2H, m); 5.95 (1H, s); 5.32 (1H, bs); 4.51 (2H, bs); 3.80 (4H, m); 2.83 (44H, m). MS: [M+H]=523.

Example 12

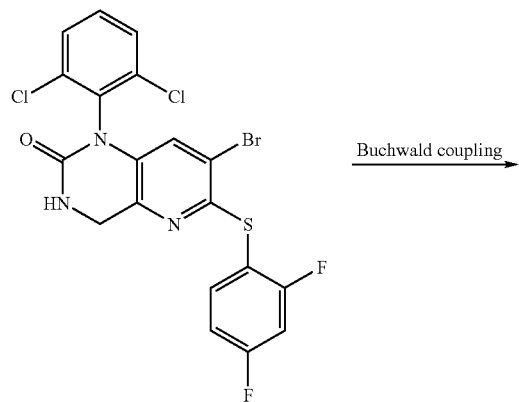

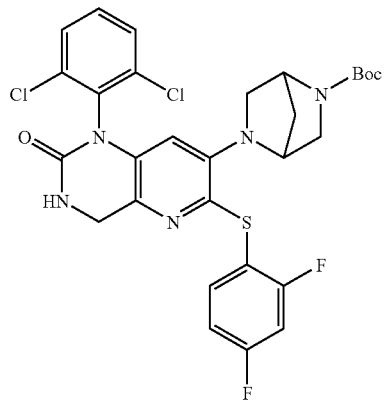

The amine coupling partner was commercially available N-Boc-bridged-piperazine. Following the general procedure the desired coupled compound was obtained. 1H NMR (CDCl, 500 MHz, ppm) 7.56-7.48 (3H, m); 7.41 (1H, t); 6.94 (2H, m); 5.89 (1H, s); 5.22 (1H, bs); 4.48 (2H, bs); 3.00-4.00 (8H, m); 1.46 (9H, s). MS: [M+H]=634

Example 13

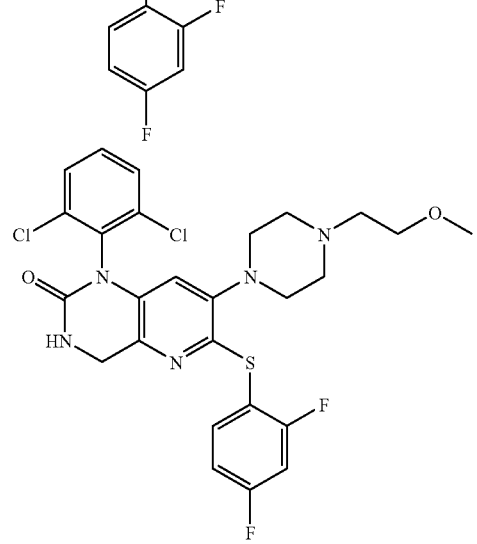

The amine coupling partner was commercially available N-(2-methoxy-ethyl)-piperazine. Following the general procedure the desired coupled compound was obtained. 1H NMR (CDCl, 500 MHz, ppm) 7.56-7.48 (3H, m); 7.41 (1H, t, J=8 Hz); 6.94 (2H, m); 6.06 (1H, s); 5.28 (1H, bs); 4.45 (2H, bs); 3.58 (2H, m); 3.41 (3H, s); 3.01 (5H, m); 2.75 (5H, m). MS: [M+H]=580.

What is claimed is:

1. A compound represented by chemical formula (I) or a pharmaceutically acceptable salt thereof:

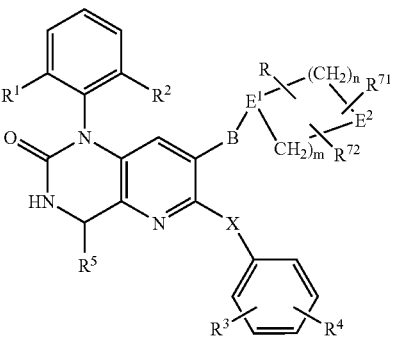

(I)

wherein
- B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-. —$C_{0-3}$alkyl-C(O)—$C_{0-3}$alkyl-, or a direct bond;
- X is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-S—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;
- R, $R^{71}$, and $R^{72}$ each independently is hydrogen, OH, or $C_{1-4}$alkyl, any alkyl optionally substituted with 1-6 groups, each group independently being —OH, —$NH_2$, —NH—$CH_3$, —N($CH_3$)$_2$, or halogen;
- n is 1, 2, 3, or 4;
- m is 0, 1, 2, 3, or 4;
- n+m is 2, 3, 4, 5, or 6; optionally, one of n $CH_2$ and one of m $CH_2$ are bridged by a —$C_{0-2}$alkyl- linkage;
- $E^1$ is CH, N, or $CR^6$;
- $E^2$ is CH2, CHR, NH, NR, O, S, —S(O)—, or —S(O)2—;
- $R^1$ is halogen or $C_{1-4}$alkyl;
- $R^2$, $R^3$, $R^4$, and $R^6$ are each independently halogen, Cl4alkyl, or hydrogen; and
- $R^5$ is H, $CH_3$, or $CH_2CH_3$.

2. The compound according to claim 1, or a pharmaceutically acceptable salt thereof wherein
   X is —$C_{0-3}$alkyl-S—$C_{0-3}$alkyl-.

3. The compound according to claim 1, or a pharmaceutically acceptable salt thereof, whereinm
   X is —$C_{0-3}$alkyl-S—$C_{0-3}$alkyl-; and
   B is a direct bond.

4. The compound according to claim 3, or a pharmaceutically acceptable salt thereof, wherein
   $E^1$ is N; and
   $E^2$ is NR.

5. The compound according to claim 3, or a pharmaceutically acceptable salt thereof; wherein
   $E^1$ is N;
   $E^2$ is NR; and
   one of n $CH_2$ and one of m $CH_2$ are bridged by a $C_{0-2}$alkyl- linkage.

6. The compound according to claim 3, or a pharmaceutically acceptable salt thereof, wherein
   $E^1$ is N; and
   $E^2$ is 0.

7. The compound according to claim 3, or a pharmaceutically acceptable salt thereof, wherein
   $E^1$ is N; and
   $E^2$ is CHR.

8. The compound according to claim 1, or a pharmaceutically acceptable salt thereof, wherein
   X is —$C_{0-3}$alkyl-S—$C_{0-3}$alkyl-; and
   B is NH.

9. The compound according to claim 8, or a pharmaceutically acceptable salt thereof, wherein
   $E^1$ is CH; and
   $E^2$ is NR.

10. The compound according to claim 1, or a pharmaceutically acceptable salt thereof, wherein
    X is —$C_{0-3}$alkyl-S—$C_{0-3}$alkyl-; and
    B is —$C_{0-3}$alkyl-O—$C_{0-3}$alkyl-.

11. The compound according to claim 1, represented by

-continued
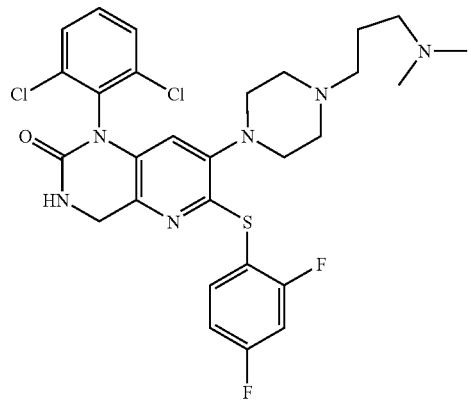
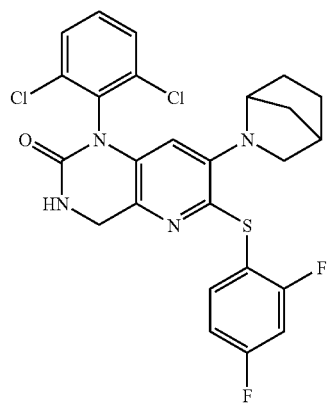
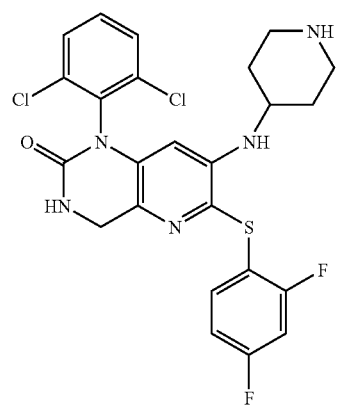
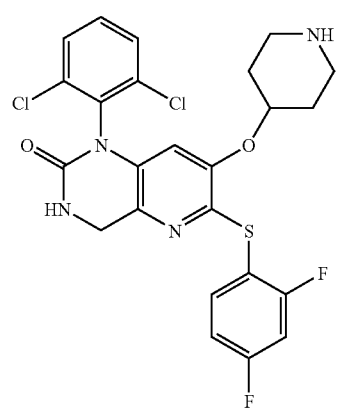
-continued
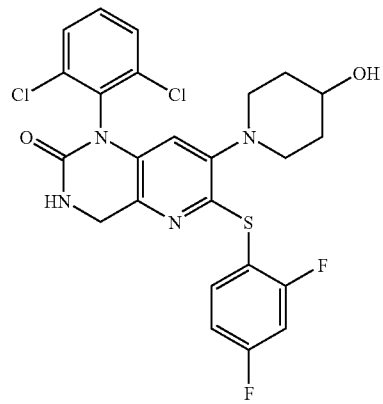
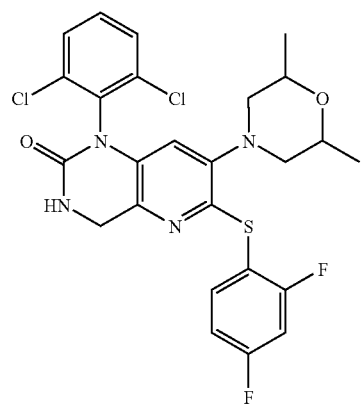
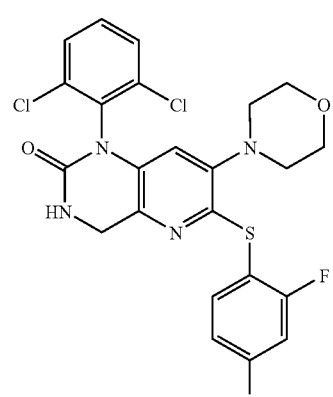

-continued
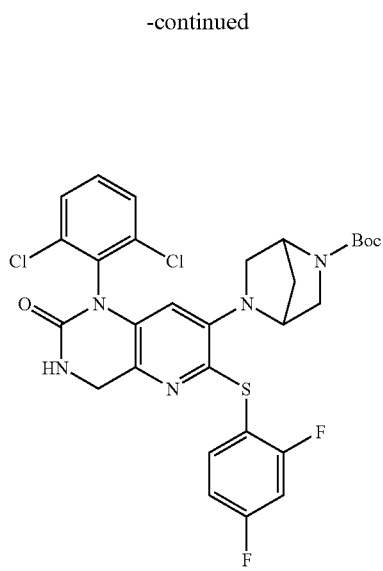
-continued
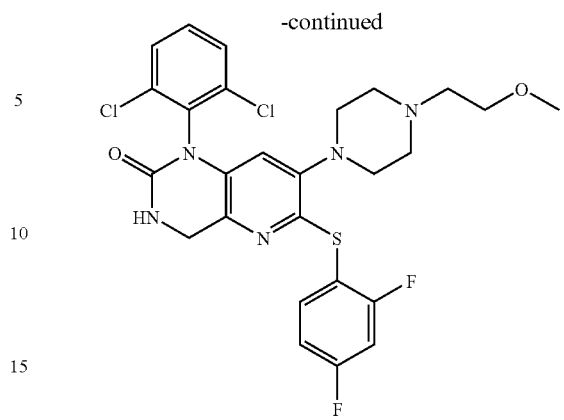
or a pharmaceutically acceptable salt thereof.
12. A pharmaceutical composition comprising an inert carrier and an effective amount of a compound according to claim 1.
* * * * *

UNITED STATES PATENT AND TRADEMARK OFFICE
CERTIFICATE OF CORRECTION

PATENT NO. : 7,314,873 B2  
APPLICATION NO. : 10/517754  
DATED : January 1, 2008  
INVENTOR(S) : Doherty et al.

Page 1 of 1

It is certified that error appears in the above-identified patent and that said Letters Patent is hereby corrected as shown below:

On cover page of the patent, in data field "(54)",

"(HALO-BENZO CARBONYL)HETEROBICYCLIC P38 LINASE INHIBITING COMPOUNDS"

Should read

-- (HALO-BENZO CARBONYL)HETEROBICYCLIC P38 KINASE INHIBITING COMPOUNDS --

Signed and Sealed this

Seventeenth Day of February, 2009

JOHN DOLL  
*Acting Director of the United States Patent and Trademark Office*

UNITED STATES PATENT AND TRADEMARK OFFICE
CERTIFICATE OF CORRECTION

PATENT NO.       : 7,314,873 B2
APPLICATION NO.  : 10/517754
DATED            : January 1, 2008
INVENTOR(S)      : Doherty et al.

It is certified that error appears in the above-identified patent and that said Letters Patent is hereby corrected as shown below:

On cover page of the patent, in data field "(54)" and Column 1, lines 1 and 2,

"(HALO-BENZO CARBONYL)HETEROBICYCLIC P38 LINASE INHIBITING COMPOUNDS"

Should read

-- (HALO-BENZO CARBONYL)HETEROBICYCLIC P38 KINASE INHIBITING COMPOUNDS --

This certificate supersedes the Certificate of Correction issued February 17, 2009.

Signed and Sealed this

Seventeenth Day of March, 2009

JOHN DOLL
*Acting Director of the United States Patent and Trademark Office*